United States Patent
Sasaki et al.

(10) Patent No.: US 7,226,437 B2
(45) Date of Patent: Jun. 5, 2007

(54) PULL-ON DISPOSABLE DIAPER

(75) Inventors: Toru Sasaki, Kagawa-ken (JP);
Shunsuke Takino, Kagawa-ken (JP);
Kyoko Ito, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 4 days.

(21) Appl. No.: 11/048,882

(22) Filed: Feb. 3, 2005

(65) Prior Publication Data

US 2005/0131375 A1  Jun. 16, 2005

Related U.S. Application Data

(63) Continuation of application No. PCT/JP03/10669, filed on Aug. 22, 2003.

(30) Foreign Application Priority Data

Aug. 30, 2002 (JP) ............................. 2002-255987

(51) Int. Cl.
*A61F 13/494* (2006.01)
*A61F 13/539* (2006.01)
(52) U.S. Cl. .................. 604/385.201; 604/385.27; 604/385.28; 604/385.29
(58) Field of Classification Search ........... 604/385.27, 604/385.28, 385.29, 385.201
See application file for complete search history.

(56) References Cited

U.S. PATENT DOCUMENTS

| 3,196,874 A |   | 7/1965  | Hrubecky |            |
|-------------|---|---------|----------|------------|
| 3,710,797 A | * | 1/1973  | Marsan   | 604/385.201|
| 3,724,464 A | * | 4/1973  | Enloe    | 604/365    |
| 3,744,494 A |   | 7/1973  | Marsan   |            |
| 3,774,610 A | * | 11/1973 | Eckert et al. | 604/365 |
| 3,848,595 A |   | 11/1974 | Endres   |            |
| 3,860,004 A |   | 1/1975  | Nystrand |            |
| 3,924,627 A |   | 12/1975 | Nystrand |            |
| 3,968,799 A |   | 7/1976  | Schrading|            |
| 4,067,336 A |   | 1/1978  | Johnson  |            |
| 4,182,334 A |   | 1/1980  | Johnson  |            |
| 4,636,207 A | * | 1/1987  | Buell    | 604/370    |
| 4,675,012 A |   | 6/1987  | Rooyakkers |          |
| 4,772,280 A |   | 9/1988  | Rooyakkers |          |
| 4,946,454 A |   | 8/1990  | Schmidt  |            |
| 5,021,051 A | * | 6/1991  | Hiuke    | 604/385.27 |
| 5,601,544 A | * | 2/1997  | Glaug et al. | 604/385.28 |

(Continued)

FOREIGN PATENT DOCUMENTS

EP    1 177 782 A1    2/2002

(Continued)

*Primary Examiner*—Tatyana Zalukaeva
*Assistant Examiner*—Paula L. Craig
(74) *Attorney, Agent, or Firm*—Lowe Hauptman & Berner, LLP

(57) ABSTRACT

A body fluid absorbing component of a pull-on disposable diaper is folded inward in a crotch covering region. Outside opposite side edges of the absorbing component, there are provided a pair of barrier walls extending in a longitudinal direction of the absorbing component. The barrier wall is provided along its zone opposed to an outer surface of the absorbing component, a distal edge of the barrier wall and an intermediate zone defined between the zone and the distal edge with first, second and third elastic members, respectively, each extending in a stretched state in the longitudinal direction of the absorbing component.

3 Claims, 8 Drawing Sheets

U.S. PATENT DOCUMENTS

| | | |
|---|---|---|
| 5,746,730 A | 5/1998 | Suzuki et al. |
| 6,102,892 A * | 8/2000 | Putzer et al. .......... 604/385.01 |
| 6,120,486 A * | 9/2000 | Toyoda et al. ......... 604/385.29 |
| 6,142,985 A * | 11/2000 | Feist ...................... 604/385.28 |
| 6,152,908 A * | 11/2000 | Widlund et al. ....... 604/385.19 |
| 6,165,160 A | 12/2000 | Suzuki et al. |
| 6,238,380 B1 * | 5/2001 | Sasaki ................... 604/385.01 |
| 6,440,117 B1 | 8/2002 | Itoh et al. |
| 6,613,955 B1 * | 9/2003 | Lindsay et al. ............. 604/378 |
| 6,666,851 B2 * | 12/2003 | Otsubo et al. ........ 604/385.201 |
| 7,112,189 B2 * | 9/2006 | Otsubo et al. ............... 604/201 |
| 7,150,729 B2 * | 12/2006 | Shimada et al. ....... 604/385.01 |
| 7,169,136 B2 * | 1/2007 | Otsubo et al. ......... 604/385.21 |
| 7,172,583 B2 * | 2/2007 | Otsubo et al. ........ 604/385.201 |
| 2002/0068919 A1 | 6/2002 | Shinohara et al. |
| 2003/0163108 A1* | 8/2003 | Tears et al. ............ 604/385.03 |
| 2004/0133178 A1 | 7/2004 | Otsubo et al. |
| 2005/0004545 A1 | 1/2005 | Shimada et al. |
| 2005/0004548 A1* | 1/2005 | Otsubo et al. ......... 604/385.25 |
| 2005/0038404 A1* | 2/2005 | Takino et al. .......... 604/385.27 |
| 2005/0131375 A1 | 6/2005 | Sasaki et al. |
| 2005/0143711 A1 | 6/2005 | Otsubo et al. |
| 2005/0148989 A1 | 7/2005 | Otsubo et al. |
| 2005/0288646 A1* | 12/2005 | Otsubo et al. ........ 604/385.201 |

FOREIGN PATENT DOCUMENTS

| | | |
|---|---|---|
| EP | 1 219 273 A2 | 7/2002 |
| JP | 47-36734 U | 12/1972 |
| JP | 48-20638 U | 3/1973 |
| JP | 50-21845 A | 3/1975 |
| JP | 50-33044 A | 3/1975 |
| JP | 56-34345 | 4/1981 |
| JP | 60-163911 | 10/1985 |
| JP | 63-32516 U | 3/1988 |
| JP | 11-188062 | 7/1999 |
| JP | 2002-035033 | 2/2002 |
| JP | 2003-010244 | 1/2003 |
| JP | 2003-220091 | 8/2003 |
| JP | 2003-230594 | 8/2003 |

* cited by examiner

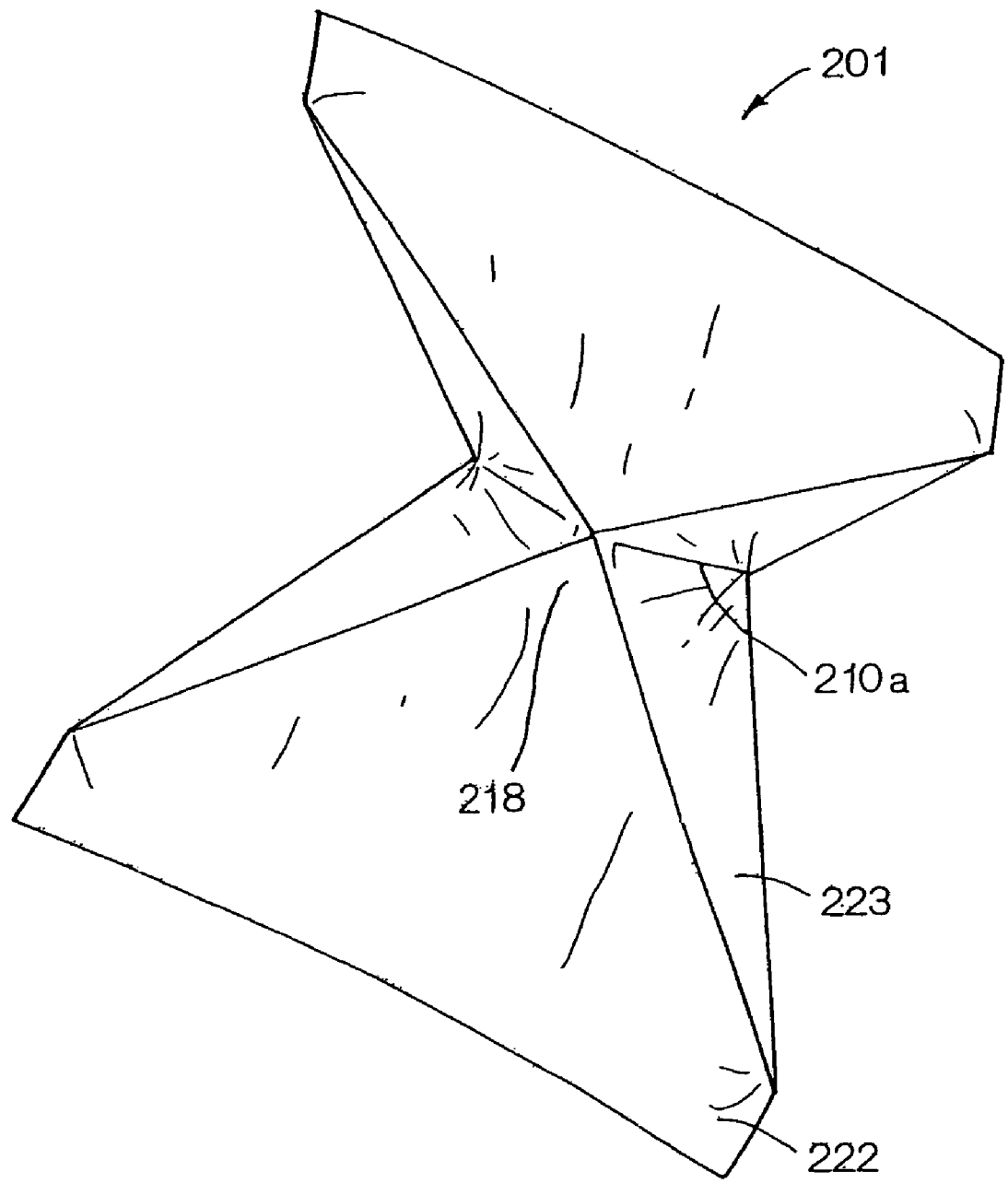

PULL-ON DISPOSABLE DIAPER

BACKGROUND OF THE INVENTION

This invention relates to a pull-on disposable diaper.

Japanese Patent Application Publication No. 1975-33044A discloses a foldup-type disposable diaper 201 as shown in FIG. 8 of the accompanying drawings. This diaper 201 is composed of a liquid-absorbent pad, a liquid-pervious inner sheet 222 and a liquid-impervious outer sheet 223 so as to present a rectangle and this rectangle is then folded along a transversal 210a orthogonal to long sides of the rectangle in two halves in a longitudinal direction. Simultaneously, the rectangle is tucked from its transversely opposite side edges inwardly of the diaper, more specifically, toward a middle point of the transversal 210a so as to form pockets 218. Surface sections of the sheet 223 facing each other as the rectangle is tucked inward in this manner are partially bonded to each other in order to prevent the respective pockets 218 might get out of initial shapes thereof even after the diaper has been developed to put the diaper on a wearer's body. The diaper arranged in such manner is effective to avoid leakage of body fluids regardless of its rectangular shape because a region of the diaper destined to cover the wearer's crotch region is sufficiently narrow to be placed closely against the wearer's crotch.

Japanese Utility Model Application Publication No. 1972-36734A discloses a foldup-type diaper made from a rectangular strip. The diaper is tucked inward from its transversely opposite edges in a longitudinally middle zone of the diaper. The crotch region of the diaper obtained in this manner has its width sufficiently reduced to be placed closely against the wearer's crotch and thereby to alleviate an anxiety of sideways urine leakage.

The diaper disclosed by Japanese Patent Application Publication No. 1975-33044A intends to prevent the diaper from getting out of its initial shape by partially bonding together the surface sections opposed to each other as the diaper is folded and tucked. However, such bonding may obstruct the diaper to be flatly developed and retard operation of putting the diaper on the wearer's body. While this conventional diaper has advantageous effects that the crotch region is folded and tucked inward so as to reduce a width of the crotch region and thereby an anxiety that the crotch region might uncomfortably compress the wearer's crotch, there is no guarantee that discharged body fluids correctly flow in an area within the crotch region folded and tucked inward. Consequently, body fluids are apt to leak sideways from the diaper.

The diaper disclosed in the above-cited Japanese Utility Model Application Publication No. 1972-36734A is accompanied with an inconvenience that the crotch region folded and tucked in this manner is apt to get out of its folded and tucked state as the diaper is put on the wearer's body.

SUMMARY OF THE INVENTION

It is an object of this invention to provide a pull-on disposable diaper improved so that, whether or not the opposite side edges of the body fluid absorbing component folded and tucked inward are bonded as in the above-cited conventional disposable diaper, the shape of the absorbing component is reliably maintained even after the diaper has been put on the wearer's body and the anxiety that folding and tucking of the crotch region might induce a leakage of body fluids.

In accordance with this invention, there is provided a pull-on disposable diaper having a height direction, a transverse direction and a longitudinal direction crossing one another, the diaper being generally symmetric about a center line bisecting a dimension of the diaper in the transverse direction, the diaper comprising a covering component having an inner surface facing a wearer's body, an outer surface facing wearer's clothes, being composed of a front waist covering region destined to cover a wearer's front waist region, a rear waist covering region destined to cover a wearer's rear waist region and a crotch covering region destined to cover a wearer's crotch region so as to define a pants-like configuration having a waist-hole and a pair of leg-holes and being provided with a body fluid absorbing component extending over the crotch covering region and further extending into the front and rear waist covering regions.

The diaper according to this invention further comprises the body fluid absorbing component comprising a liquid-absorbent core and a liquid-pervious cover sheet and having an inner surface facing the wearer's body, an outer surface which is a reverse side of the inner surface and lateral edge zones connecting the inner and outer surfaces to each other and extending beyond the crotch covering region into the front and rear waist covering regions, the cover sheet covering the inner surface of the core, the lateral edge zone of the core and at least a part of the outer surface of the core, the body fluid absorbing component being formed in the crotch covering region with a first folding guide extending from a middle zone between the lateral edge zones of the absorbing component to respective the lateral edge zones in the front waist covering region so as to describe a generally V-shape, a second folding guide extending to respective the lateral edge zones in the rear waist covering region so as to describe a generally V-shape and a third folding guide extending in the transverse direction between the first and second folding guides, and the absorbing component being folded on both sides of the center line along the third folding guide so that the core has its outer surface sections facing to each other and along the first and second folding guides so that the core has its inner surface sections facing to each other; a pair of barrier walls provided outside the side edges of the absorbing component, respectively, and extending along the lateral edge zones of the absorbing component in the longitudinal direction, each of the barrier walls having an inner edge zone lying inside in the width direction and an outer edge zone lying outside in the width direction, the inner edge zone being secured to one of a sheet defining the crotch covering region of the absorbing component and the cover sheet in the vicinity of the center line so as to be substantially fixed to the absorbing component, the outer edge zone being let free from the absorbing component so as to be deformable independent of the absorbing component, the barrier wall having longitudinally opposite ends secured to one of a sheet defining the front and rear waist covering regions on the outer surface of the absorbing component and the cover sheet, the barrier wall having an intermediate zone defined between the inner edge zone and the outer edge zone as viewed in the transverse direction and folded toward the center line and thereafter having been secured to the inner surface of absorbing component so that the outer edge zone lies outside in the transverse direction, layers of the barrier wall placed upon each other being secured to each other; and elastic members being attached to the outer edge zone, a vicinity of a zone along which the barrier wall is folded outward in the transverse direction and an area of the inner edge zone in which the barrier wall is let free from the absorbing component in a stretched state so as to extend between the longitudinally opposite ends of the barrier wall, the barrier wall being elastically contractible in the longitudinal direction in the crotch covering region.

This invention includes the following embodiments.

The outer surface of the core has a transversely middle zone formed by a liquid-impervious sheet.

The diaper further comprises a nonwoven fabric lying outside the outer surface of the absorbing component and the liquid-impervious sheet formed by plastic film lying outside the nonwoven fabric.

BRIEF DESCRIPTION OF THE DRAWINGS

FIG. 8 is a perspective view showing an example of the conventional diaper.

DETAILED DESCRIPTION OF THE PREFERRED EMBODIMENTS

Details of the pull-on disposable diaper according to this invention will be more fully understood from the description given hereunder with reference to the accompanying drawings.

Figure 1:
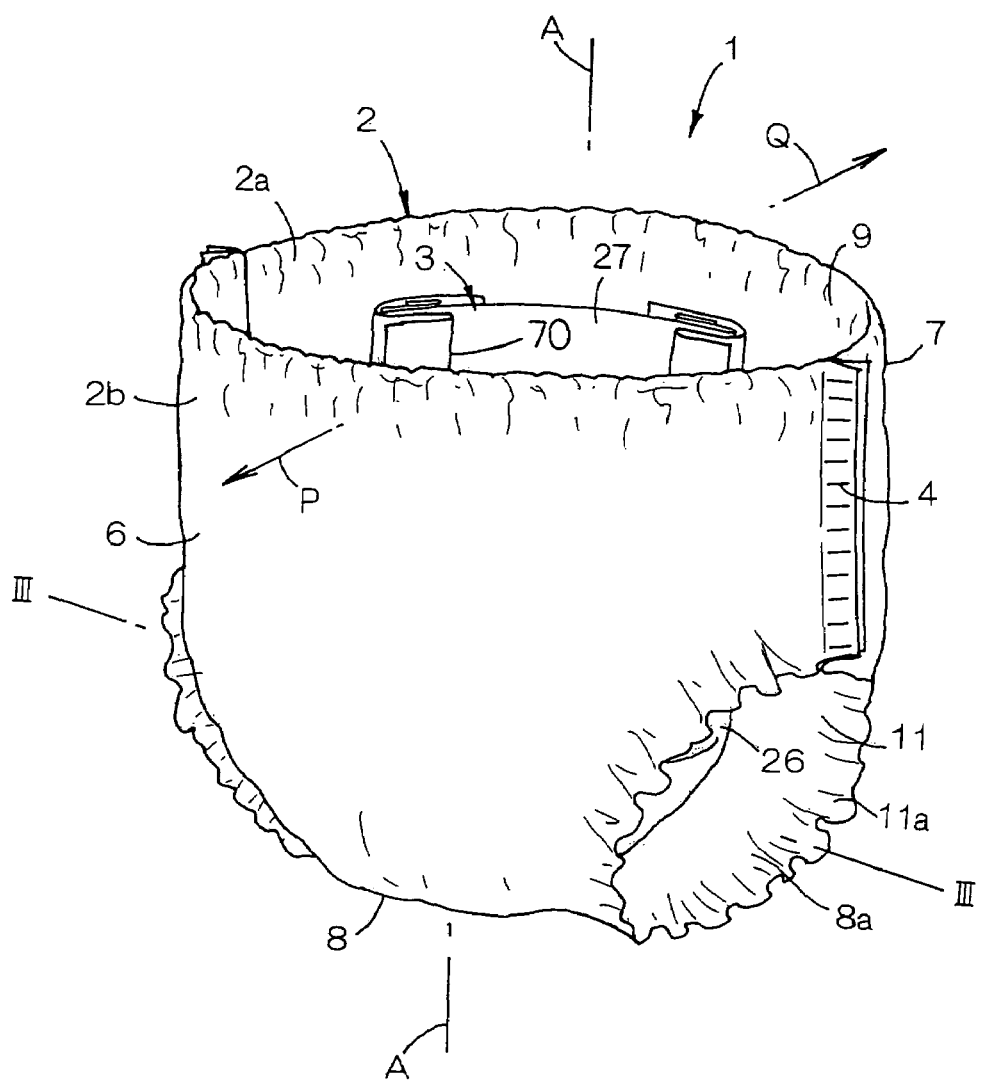
FIG. 1 is a perspective view showing a pull-on disposable diaper.
Figure 2:
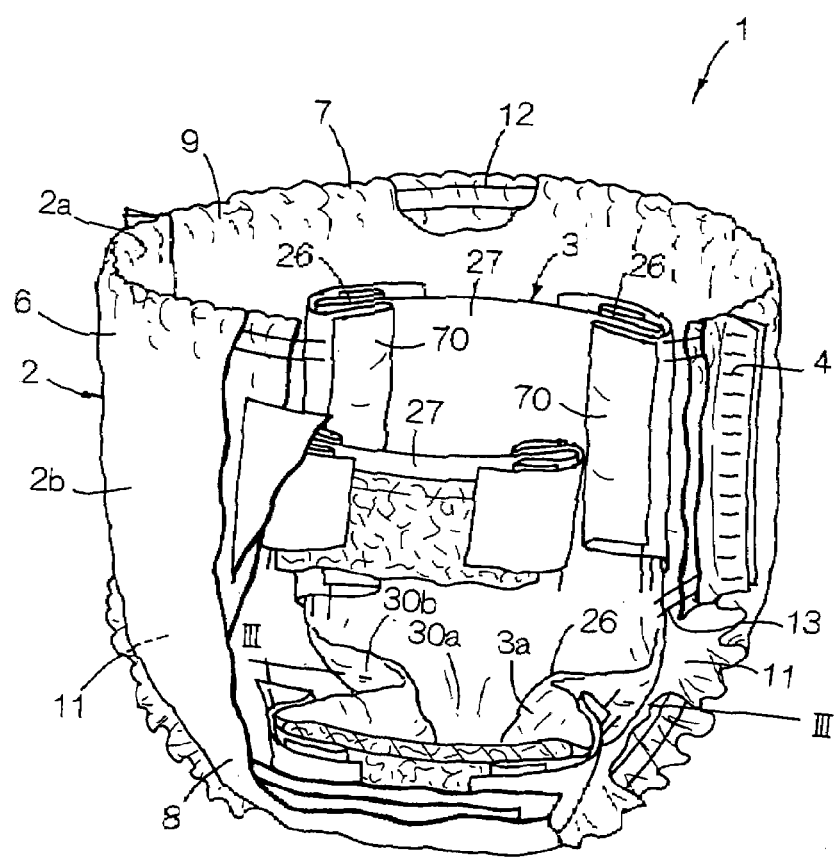
FIG. 2 is a partially cutaway perspective view showing the diaper of FIG. 1.
Figure 3:
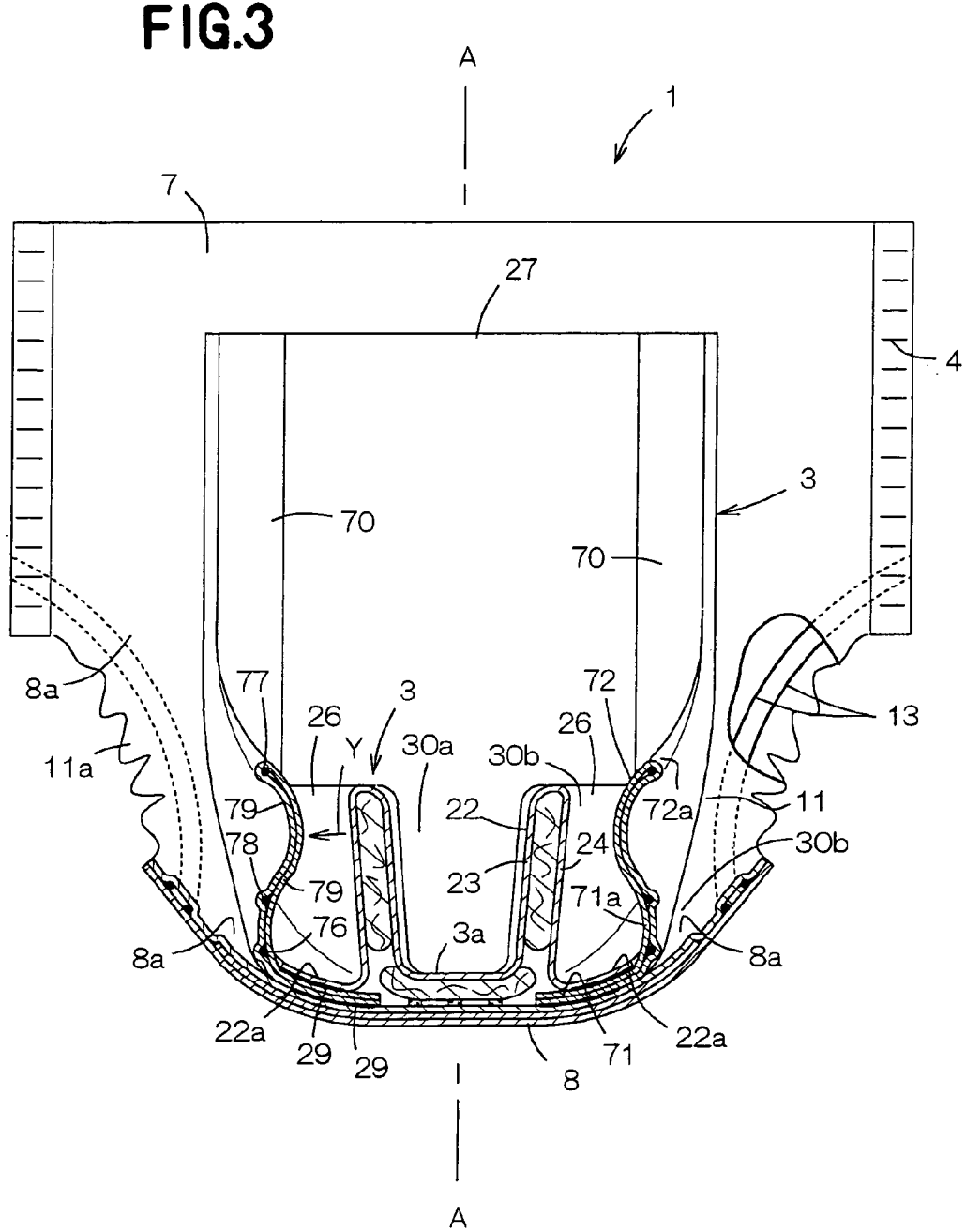
FIG. 3 is a sectional view taken along a line III—III in FIG. 1.

FIG. 1 is a perspective view showing a pull-on disposable diaper 1, FIG. 2 is a partially cutaway perspective view showing this diaper 1 and FIG. 3 is a sectional view taken along a line III—III in FIG. 1. The diaper 1 has height and width directions orthogonal to each other and a back-and-forth direction. The height direction corresponds to a vertical direction in FIG. 1, the back-and-forth direction corresponds to a direction indicated by a double-headed arrow P-Q in FIG. 1 and the width direction corresponds to a right-and-left direction as viewed in FIG. 3. The diaper 1 basically comprises a pants-like covering component 2 and a body fluid absorbing component 3 serving also to contain body fluids absorbed therein. The covering component 2 is formed by sheet material such as a nonwoven fabric or a plastic film. The covering component 2 has an inner surface 2a facing a diaper wearer's body and an outer surface 2b facing wearer's clothes. This covering component 2 is composed of a front waist covering region 6, a rear waist covering region 7 and a crotch covering region 8 adapted to cover a front waist, a rear waist and a crotch of a wearer, respectively. The front and rear waist covering regions 6, 7 are overlaid and joined together at a plurality of joining zones 4 arranged intermittently in the vertical direction along transversely opposite lateral marginal edges so that the front waist covering region 6, the rear waist covering region 7 and the crotch covering region 8 cooperate one with another to define a waist-hole 9 and a pair of leg-holes 11. The waist-hole 9 and the leg-holes 11 are provided along peripheral marginal edges thereof with a plurality of waist-surrounding elastic member 12 and a plurality of thigh-surrounding elastic members 13 attached thereto in a stretched state, respectively. The body fluid absorbing component 3 transversely opposite side edges 26 lying on the inner surface 2a of the covering component 2 so as to extend in the crotch covering region 8 further into the front and rear waist covering regions 6, 7 and longitudinally opposite ends 27 lying on the inner surface 2a of the covering component 2 so as to extend in the waist-circumferential direction in the front and rear waist covering regions 6, 7. The body fluid absorbing component 3 is folded toward a longitudinal center line A—A (See FIG. 4 also) bisecting a width of the diaper 1, i.e., folded inward in a transverse direction of the diaper 1 so that the body fluid component 3 may have its width reduced in the crotch covering region 8. The body fluid absorbing component 3 further includes barrier walls 70 lying outside the transversely opposite side edges 26 so as to extend toward the longitudinally opposite ends 27.

Figure 4:
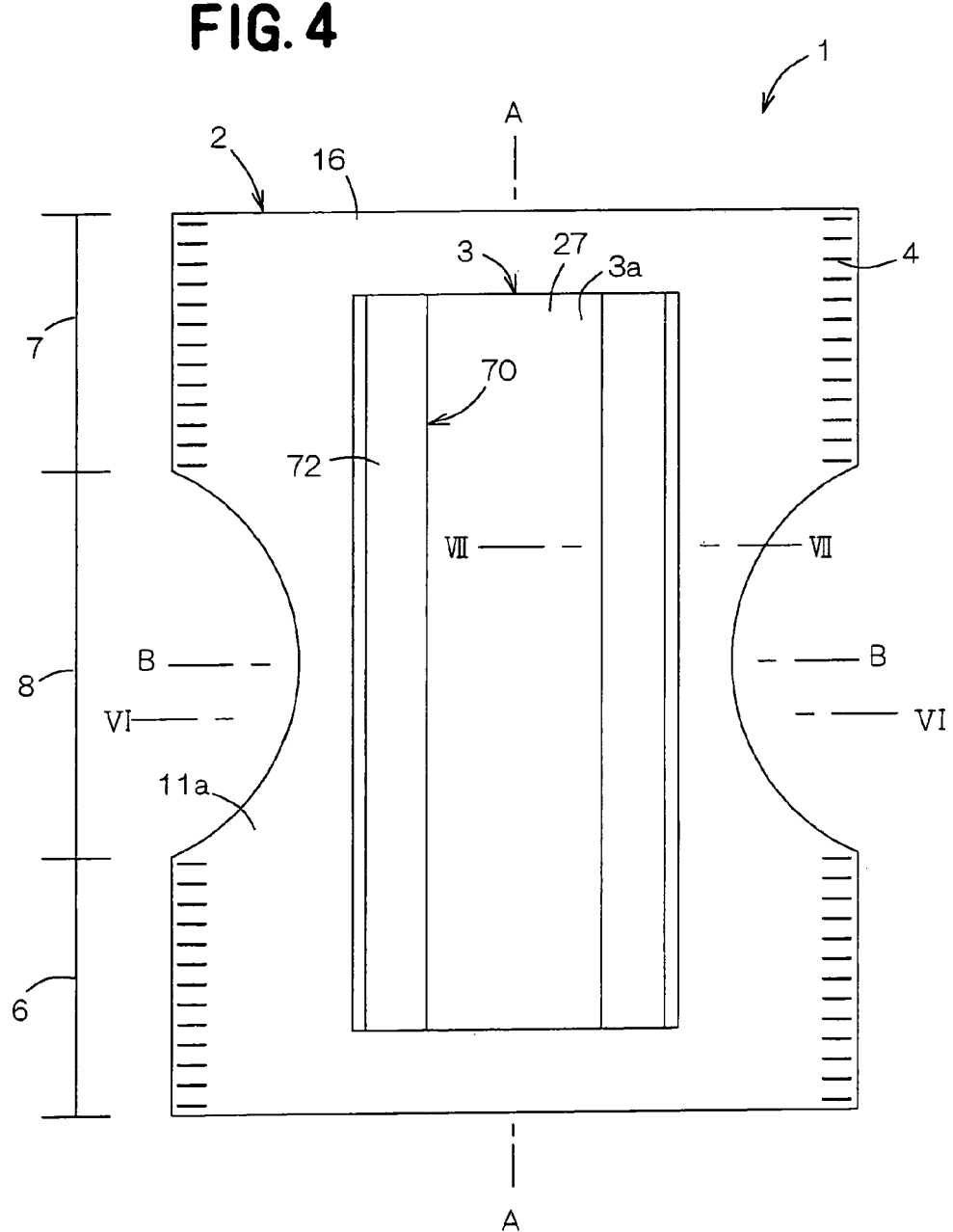
FIG. 4 is a developed view of the diaper of FIG. 1.
Figure 5:
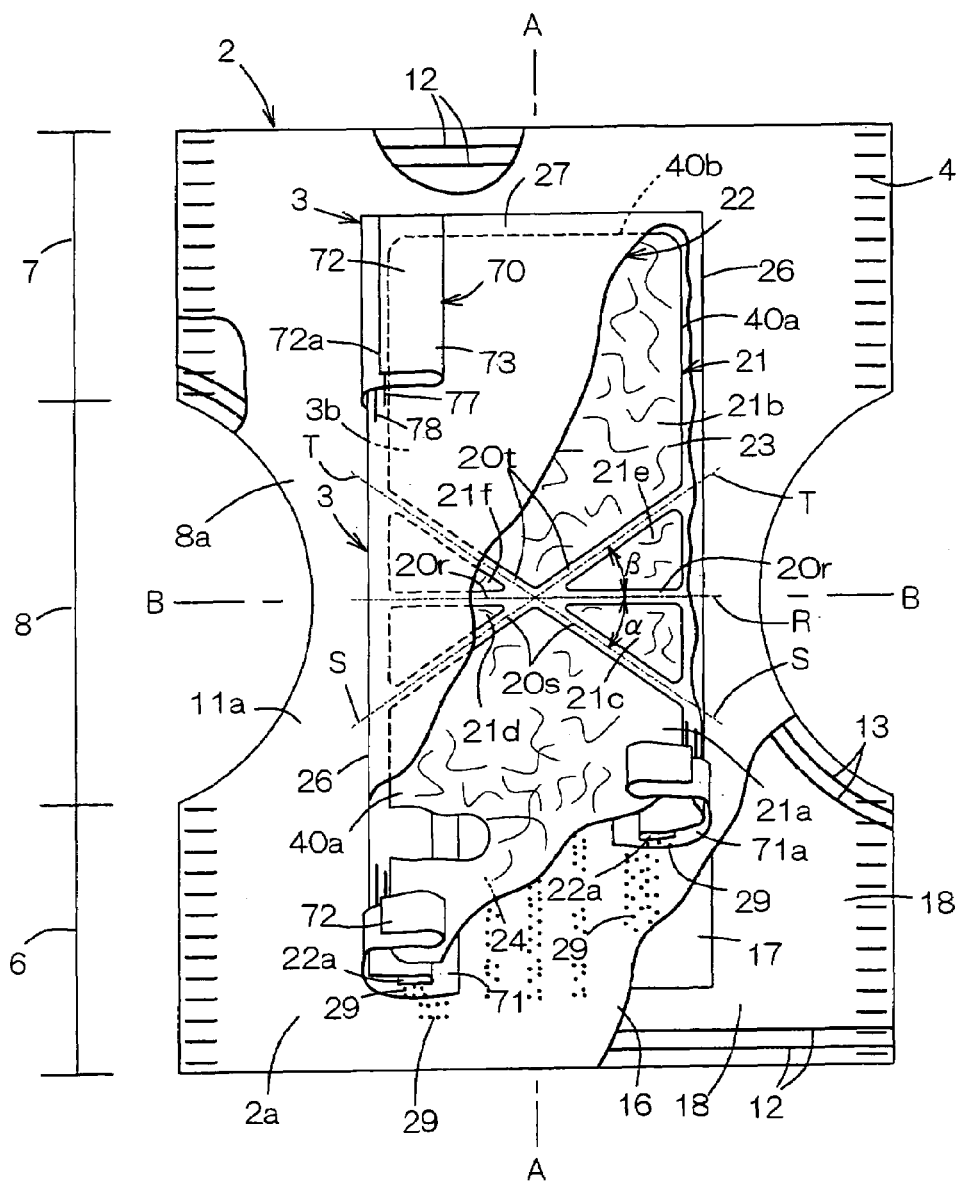
FIG. 5 is a partially cutaway view similar to FIG. 4, showing the diaper.
Figure 6:
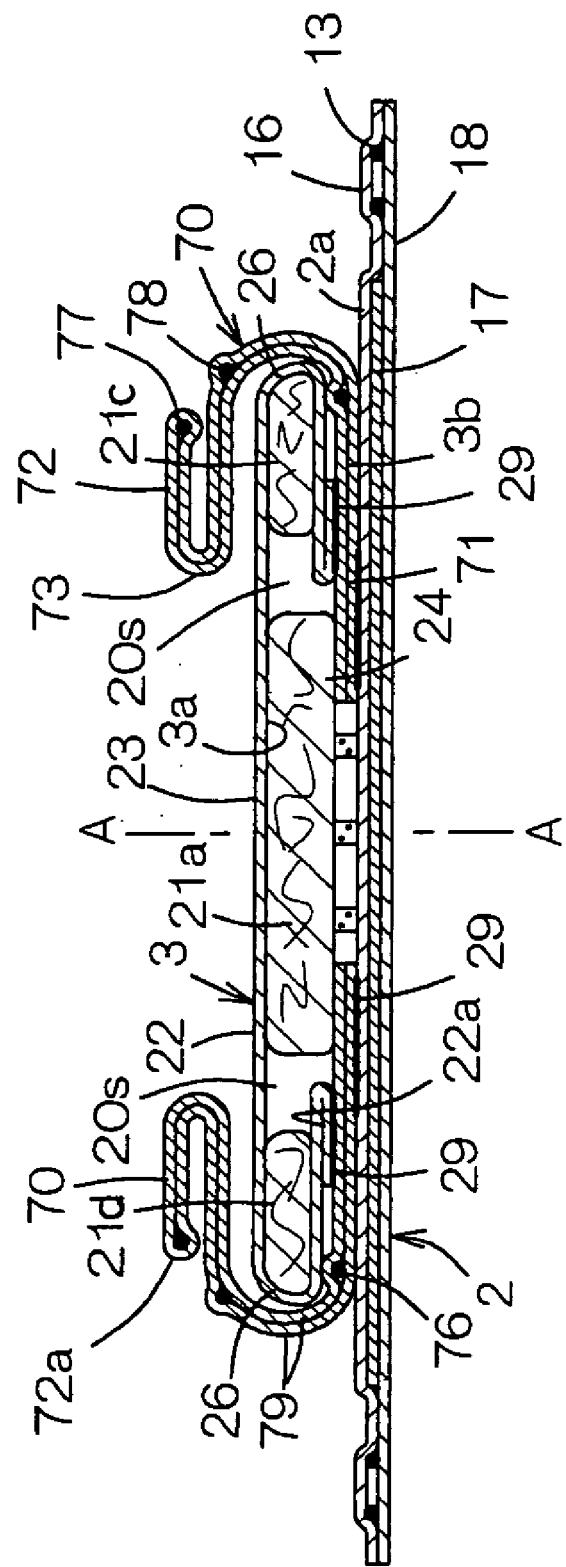
FIG. 6 is a sectional view taken along a line V—V in FIG. 4.

FIG. 4 is a plan view of the diaper 1 of FIG. 1 with the front and rear waist covering regions 6, 7 disconnected each other along respective arrays of the joining zones 4 and developed for- and backward, respectively, as indicated by arrows P, Q, FIG. 5 is a partially cutaway view similar to FIG. 4, showing the diaper 1 and FIG. 6 is a sectional view taken along a line V—V in FIG. 4. In FIGS. 4–6, a transverse center line B—B extends in a direction orthogonal to the longitudinal center line A—A so as to bisect a length of the developed diaper 1. In the developed state as shown in FIG. 4, the diaper 1 is generally symmetric about the longitudinal center line A—A and may be folded back along the transverse center line B—B to obtain the diaper 1 in the state as shown in FIG. 1.

The covering component 2 comprises a laminate of an inner sheet 16, an intermediate sheet 17 and an outer sheet 18 which are overlaid and joined to one another intermittently. The inner sheet 16 has an hourglass-shape and is formed by breathable nonwoven fabric, more preferably, formed by hydrophobic but breathable nonwoven fabric. The intermediate sheet 17 has a size substantially same as or larger than a size of the planer absorbing component 3 and is formed by liquid-impervious plastic film, more preferably, formed by breathable but liquid-impervious plastic film. The outer sheet 18 has the same size as the inner sheet and is formed by breathable nonwoven fabric. The waist- and thigh-surrounding elastic members 12, 13 interposed between the inner and outer sheets 16, 18 are secured to at least one of these sheets 16, 18 by means of an adhesive agent (not shown).

The absorbing component 3 comprises a core 21 and a cover sheet 22 and is formed on both sides with barrier walls 70, respectively. The absorbing component 3 has a rectangular shape which is relatively long in the vertical direction as viewed in FIGS. 4 and 5. This rectangular absorbent component 3 is contoured by the transversely opposite side edges 26 extending parallel to the longitudinal center line A—A and the longitudinally opposite ends 27 extending in the waist-circumferential direction so as to cross the transversely opposite side edges 26. The core 21 has a rectangular shape as a whole and has an inner surface 23 facing the wearer's body, an outer surface 24 facing the wearer's clothes, opposite side edges 40a extending in the longitudinal direction and opposite ends 40b extending in the waist-circumferential direction. The core 21 additionally has grooves 20r, 20s, 20t extending along a chain line R (third folding guide) which is coincidence with the transverse center line B—B, a chain line S (first folding guide) extending from a central zone of the core 21 defined by the intersection of the longitudinal center line A—A and the transverse center line B—B to the opposite side edges 40a so as to describe a V-shape in the front waist covering region 6 and a chain line T (second folding guide) extending from the central zone of the core 21 so as to describe a V-shape to the opposite side edges 40b in the rear waist covering region 7. These grooves 20r, 20s, 20t divide the core 21 into core elements 21a, 21b, 21C, 21d, 21e, 21f. The groove 20r and the groove 20s intersect with each other at an angle α while the groove 20r and the groove 20t intersect with each other at an angle β. The angles α and β are illustrated to be equal to each other. In the crotch covering region 8, the absorbing component 3 is narrower than the covering component 2. As will be apparent from FIGS. 1, 2 and 3, lateral marginal portions 8a of the covering component 2 in the crotch covering region 8 defining leg-holes 11 lie on the side of the outer surface 3b of the absorbing component 3 and extend outward beyond the side edges 26 of the absorbing component 3 to form thigh-surrounding flaps 11a defining the respective leg-holes 11.

Each core element 21a through 21e is formed by compressing water-absorbent materials such as fluff pulp and super-absorbent polymer particles under an appropriate pressure and, if desired, covering such compressed materials with a tissue paper or a nonwoven fabric of thermoplastic synthetic fibers modified to be hydrophilic. The inner surface 23 of the core element 21a through 21f or the tissue paper or the like (not shown) covering this inner surface 23 may be secured to the cover sheet 22. The outer surface 24 of the core element 21a through 21f or the tissue paper or the like covering this outer surface 24 may be secured to the inner sheet 16.

The cover sheet 22 extends in the transverse direction of the core 21 so as to cover the inner surface 23 of the core element 21a through 21f, and further extends beyond the side edges 40a so as to cover the outer surface 24 in the vicinity of the respective side edges 40a. On the outer surface 24, lateral edge zones 22a of the cover sheet 22 are folded outward in the transverse direction of the core 21 and secured to the barrier walls 70 by means of a hot melt adhesive agent 29. The opposite end portions 27 of the absorbing component 3 extending beyond the longitudinally opposite ends 40b of the core 21 are secured to the inner sheet 16 by means of a hot melt adhesive agent (not shown). Such cover sheet 22 is folded in a Z-shape or in an inverted Z-shape in the vicinity of the side edges 40a of the core 21 (See FIGS. 5 and 6). A stock material for the cover sheet 22 may be selected from the group consisting of a liquid-pervious nonwoven fabric, a perforated plastic film and a laminated sheet of these nonwoven fabric and film.

Figure 7:
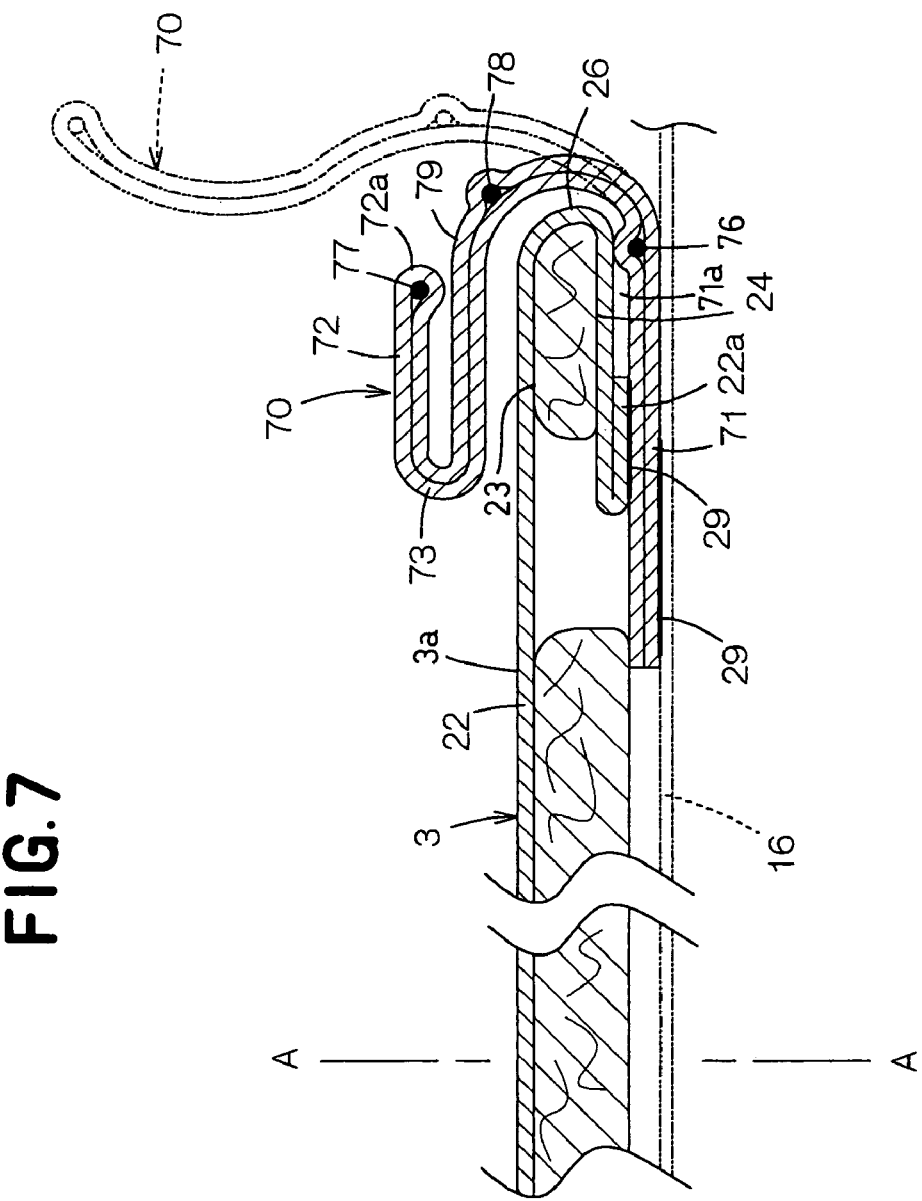
FIG. 7 is a sectional view taken along a line VII—VII in FIG. 4.

FIG. 7 is a sectional view taken along a line VII—VII in FIG. 4, illustrating one of the barrier walls 70 in the crotch covering region 8. The barrier wall 70 indicated by imaginary lines corresponds to the barrier wall 70 as shown in FIG. 3. The barrier wall 70 is formed by a sheet 79 made of nonwoven fabric or plastic film, preferably a liquid-impervious sheet, more preferably a breathable but liquid-impervious sheet. In the case of the illustrated embodiment, such sheet 79 is folded in two layers to form the barrier wall 70 having an inner edge zone 71 and an outer edge zone 72 both extending parallel to the longitudinal center line A—A. The inner edge zone 71 is laid on the outer surface 24 of the absorbing component 3 and secured to the folded lateral edge zone 22a of the cover sheet 22 and to the inner sheet 16 by means of an adhesive 29 or a heat-sealing technique while the barrier wall 70 is let free from the outer surface 24 of the absorbing component 3 in the vicinity of the side edges 26 (See FIG. 3). In the transverse direction of the absorbing component 3, the barrier wall 70 is folded back along the side edge 26 of the absorbing component 3 from the side of its outer surface 24 to the side of its inner surface 23 so as to be directed toward the longitudinal center line A—A and then, folded back again along its transversely intermediate zone 73 so that the outer edge zone 72 lies outside in the transverse direction of the absorbing component 3 so as to have a Z-shaped or an inverted Z-shaped cross-section. In the vicinity of the opposite ends 27 of the absorbing component 3, the barrier wall 70 folded in this manner is secured to the cover sheet 22 defining the inner surface of the absorbing component 3 and to the layers of the barrier wall 70 itself placed upon each other. In the crotch covering region 8, on the other hand, the inner edge zone 71 of the barrier wall 70 is secured merely to the lateral edge zone 22a of the cover sheet 22 and to the inner sheet 16 but neither to an inner surface 3a of the absorbing component 3 nor to the layers of the barrier wall 70 itself placed upon each other, as will be apparent from FIG. 7. The barrier wall 70 is provided along an area 71a of the inner edge zone 71 spaced apart from the outer surface 24 of the absorbing component 3, a distal edge 72a of the outer edge zone 72 and in the vicinity of the intermediate zone 73 along which the outer edge zone 72 is folded back outward with first, second and third elastic members 76, 77, 78, respectively, each comprising at least a single elastic element, as will be seen in FIGS. 3 and 4. These elastic members 76, 77, 78 are in a stretched state between the longitudinally opposite ends 27, 27 of the absorbent component 3 and secured to the inner surface of at least one of the sheets 79, 79 placed upon each other.

The diaper 1 having the absorbing component 3 as shown in FIG. 4 is folded along the transverse center line B—B as well as the longitudinal center line A—A as shown in FIGS. 2 and 3 to obtain the diaper 1 in which the front and rear waist covering regions 6, 7 are joined to each other at the joining zones 4 as shown in FIG. 1. Specifically, the absorbing component 3 is folded along the groove 20r so that the outer surface 24 of the core element 21c is opposed to the outer surface 24 of the core element 21e (See FIGS. 3 and 6) while the outer surface 24 of the core element 21d is opposed to the outer surface 24 of the core element 21f. At the same time, the absorbing component 3 is folded along the grooves 20s, 20t so that the inner surface 23 of the core element 21a is opposed to the inner surfaces 23 of the respective core elements 21c, 21d while the inner surface 23 of the core element 21b is opposed to the inner surfaces 23 of the respective core elements 21e, 21f. More specifically, in the portions of placed aside toward its front and rear ends, respectively, the absorbing component 3 is folded along the respective folding guides each extending from the transversely middle zone to each of the side edges 26 of the absorbing component 3 so as to describe a generally V-shape. In the grooves 20r, 20s, 20t of the absorbing component 3, there is no or less core 21 so the absorbing component 3 has its stiffness lower in these grooves 20r, 20s, 20t than in other regions. This unique arrangement facilitates the absorbing component 3 to be folded along the grooves 20r, 20s, 20t as shown in FIG. 2.

The first, second and third elastic members 76, 77, 78 contract as the absorbent component 3 is folded back along the transverse center line B—B and tucked toward the longitudinal center line A—A and thereby each of the barrier walls 70 rises in the front and rear waist covering regions 6, 7 and the crotch covering region 8, at least in the crotch covering region 8. Referring to FIGS. 2 and 3, the first and third elastic members 76, 78 lie on the lateral side of the absorbing component 3 rising above the inner surface of the covering component 2 in the crotch covering region 8 and bias the portions of the absorbing component 3 which have been folded toward the longitudinal center line A—A to draw near to each other in the direction opposite to the direction indicated by the arrows P, Q, i.e., inwardly as viewed in the back-and-forth direction. In this way, the first and third elastic members 76, 78 prevent the portions having been folded toward the center line A—A from being unfolded in the direction indicated by the arrows P, Q. Particularly, the first elastic member 76 lying on the side of the outer surface 24 of the absorbing component 3 extends across the grooves 20r, 20s, 20t and has its effectively stretched length is limited to almost the crotch covering region 8. In an advantageous consequence, the portions of the absorbing component 3 which have been folded are easily kept in a folded state even when the diaper 1 is put on the wearer's body. In addition, the barrier walls 70 are kept flat without following the absorbing component 3 while the barrier wall 70 is formed with fine gathers. The second elastic members 77 lie in the vicinity of the respective side edges 26 of the absorbing component 3 and thereby function to ensure that the barrier walls 70 can be spaced apart from each other by a dimension larger than the dimension between the side edges 26 of the absorbing component 3 folded toward each other and at the same time the outer edge zones 26 can closely contact with the wearer's thighs. Thus the second elastic member 77 reliably prevents body fluids from leaking sideways from the diaper 1 even if body fluids do not flow into the region defined between the opposite side edges 26, 26. The third elastic member 78 effectively biases the intermediate zone 73 of the barrier wall 70 defined between the first elastic member 76 and the second elastic member 77 to rise above the inner surface of the crotch covering region 8.

In the pull-on disposable diaper 1 arranged as has been described, the opposite side edges 26, 26 of the absorbing component 3 is folded so that the width of the absorbing component 3 may be reduced in the crotch covering region 8, as will be apparent from FIG. 3, and those opposite side edges 26, 26 extending upward may advantageously closely contact with the wearer's crotch in the vicinity of the wearer's genital organs. Consequently, discharged urine is immediately absorbed by the diaper 1 without spreading in the transverse direction. In addition, a space defined between these opposite side edges 26, 26 forms a pocket 30a depressed downward serving to prevent a possibility that the inner surface 3a of the absorbent component 3 wetted with absorbed urine might closely contact with the wearer's body over a large area and provide the wearer with an discomfortable feeling. Even if the body fluids flow beyond the side edges 26, the barrier walls 70 lying outside the opposite side edges 26 and adapted to tightened around the wearer's thighs bank up further flowing of body fluids. Such arrangement reliably eliminates an anxiety that body fluids might leak out from the diaper 1. Furthermore, the outer surface 24 of the absorbent component 3 is covered with the liquid-pervious cover sheet 22 at least in the vicinity of the side edges 26, so if any amount of body fluids flow beyond the side edges 26, such amount of body fluids will be introduced into outer pockets 30b (See FIG. 3) formed between the absorbing component 3 and the barrier walls 70 and absorbed by the core 21 through its outer surface 24. It should be noted here that the outer surface 24 of the core 21 may be at least partially, for example, in its transversely middle zone, covered with a liquid-impervious intermediate sheet, as shown in FIG. 3.

In this diaper 1, in addition to the function of the first and third elastic members 76, 78, the lateral edge zones 22a of the cover sheet 22 is folded outward in the transverse direction of the absorbing component 3 and secured to the sheets 79 of the barrier walls 70, as will be apparent from FIGS. 3 and 5 and therefore movement of the core elements 21c, 21e ; 21d, 21f having been folded along the groove 20r tending to restore the state of these core elements before folded, in other words, move outward with respect to the diaper 1 is restrained. The first and third elastic members 76, 78 cooperate with the lateral edge zones 22a to restrain such movement and thereby to facilitate the absorbing component 3 to be kept in the folded configuration even after the diaper 1 has been put on the wearer's body.

Depending on a thickness of the core 21, it is possible to eliminate the groove 20r and to use only the grooves 20s, 20t in order to fold the absorbing component 3 as shown in FIG. 2. It is also possible to fold the absorbing component 3 using a zone having a stiffness higher than that in the other zone. The zone is formed by pressing the absorbing component 3 locally along the chain lines R, S, T or the chain lines S, T using embossing rolls or the like with or without heating the zone.

The pull-on disposable diaper according to this invention has advantageous effects that the shape of the absorbing component after having been folded can be reliably kept and any amount of body fluids having flown outward beyond the side edges of the absorbing component can be banked up by the barrier walls so as to avoid sideways leakage of body fluids reliably because the transversely opposite side edges of the body fluid absorbing component are folded inward in the transverse direction of the absorbing component in the crotch covering region so as to reduce the width thereof, and outside the respective side edges there are provided the barrier walls, respectively, adapted to be elastically contractible in the longitudinal direction of the absorbing component.

What is claimed is:

1. A pull-on disposable diaper having a transverse direction and a longitudinal direction crossing one another, said diaper being generally symmetric about a center line bisecting a dimension of the diaper in said transverse direction, said diaper comprising:
    a covering component having:
        an inner surface adapted to face a wearer's body, and an outer surface adapted to face away from the wearer's body, and
        a front waist covering region adapted to cover the wearer's front waist region, a rear waist covering region adapted to cover the wearer's rear waist region, and a crotch covering region adapted to cover the wearer's crotch region so as to define a pants-like configuration having a waist-hole and a pair of leg-holes;
    a body fluid absorbing component extending over said crotch covering region and further into said front and rear waist covering regions, said body fluid absorbing component comprising:
        a liquid-absorbent core and a liquid-pervious cover sheet,
        an inner surface adapted to face said wearer's body, an outer surface which is a reverse side of said inner surface, and lateral edge zones connecting said inner and outer surfaces to each other and extending beyond said crotch covering region into said front and rear waist covering regions, and said cover sheet defining said inner surface of said absorbing component, said lateral edge zones of said absorbing component, and at least a part of said outer surface of said absorbing component;

said body fluid absorbing component being formed in said crotch covering region with
- a first folding guide extending from a middle zone between said lateral edge zones of said absorbing component to respective said lateral edge zones in said front waist covering region so as to describe a generally V-shape,
- a second folding guide extending to respective said lateral edge zones in said rear waist covering region so as to describe a generally V-shape,
- a third folding guide extending in said transverse direction between said first and second folding guides, and
- said absorbing component being folded on both sides of said center line along said third folding guide so that said core has its outer surface sections facing to each other, and further along said first and second folding guides so that said core has its inner surface sections facing to each other; and a pair of barrier walls provided outside said lateral edge zones of said absorbing component, respectively, and extending along said lateral edge zones of said absorbing component in said longitudinal direction, each of said barrier walls having:
- an inner edge zone and an outer edge zone located outwardly of said inner edge zone as viewed in said transverse direction;
- said inner edge zone being secured to one of (i) a sheet defining said crotch covering region of said covering component and (ii) said cover sheet in a vicinity of said center line so as to be substantially fixed to said absorbing component,
- said outer edge zone being free of direct securement to said absorbing component so as to be deformable independently of said absorbing component,
- longitudinally opposite ends secured to one of (i) a sheet defining said front and rear waist covering regions and (ii) said cover sheet,
- an intermediate zone defined between said inner edge zone and said outer edge zone as viewed in said transverse direction, and folded toward said center line,
- in a vicinity of said longitudinally opposite ends, said folded barrier wall being secured to said inner surface of said absorbing component, and layers of said folded barrier wall placed upon each other being secured to each other, and
- elastic members being attached, in a stretched state, to (i) said outer edge zone, (ii) a vicinity of a zone along which said barrier wall is folded outward in said transverse direction, and (iii) an area of said inner edge zone in which said barrier wall is free of direct securement to said absorbing component so as to extend between said longitudinally opposite ends of said barrier wall, said barrier wall being elastically contractible in said longitudinal direction in said crotch covering region.

2. The disposable diaper according to claim 1, wherein said outer surface of said absorbing component has a transversely middle zone formed by a liquid-impervious sheet.

3. The disposable diaper according to claim 2, further comprising a nonwoven fabric lying outside said outer surface of said absorbing component, wherein said liquid-impervious sheet is formed by a plastic film lying outside said nonwoven fabric.

* * * * *